United States Patent [19]

Lukas et al.

[11] Patent Number: 4,983,765

[45] Date of Patent: Jan. 8, 1991

[54] PROCESS TO SEPARATE MIXTURES OF ENANTIOMERIC ARYLPROPIONIC ACIDS

[75] Inventors: Helmut Lukas, Neu-Isenburg; Otto Schuster, Bad Soden; Gunther Rau, Kriftel, all of Fed. Rep. of Germany

[73] Assignee: PAZ Arzneimittel-Entwicklungsgesellschaft mbH, Frankfurt am Main, Fed. Rep. of Germany

[21] Appl. No.: 372,088

[22] Filed: Jun. 27, 1989

[30] Foreign Application Priority Data

Jul. 19, 1988 [DE] Fed. Rep. of Germany ....... 3824353

[51] Int. Cl.[5] .............................................. C07B 57/00

[52] U.S. Cl. .................................... 562/401; 562/402; 562/460; 562/492; 562/496

[58] Field of Search ............... 562/401, 402, 460, 492, 562/496

[56] References Cited

U.S. PATENT DOCUMENTS 4,515,811 5/1985 Holton ................................ 514/554

4,752,417 6/1988 Inoue et al. ..................... 562/401 X

*Primary Examiner*—Werren B. Lone

*Assistant Examiner*—Vera C. Clarke

*Attorney, Agent, or Firm*—Fidelman & Wolffe

[57] ABSTRACT

A process is described in which a mixture of enantiomeric arylpropionic acid is split and one of enantiomeric forms of the acid is recovered. The mixture is transformed into a diastereoisomeric salt by a reaction with a chiralic base and an inert solvent, and the desired acid enantiomer is removed from the reaction product. The transformation to a diastereoisomeric salt takes place in a polar solvent. The salt produced is recrystallized several times and the thus purified salt is split in a dilute mineral acid.

15 Claims, No Drawings

PROCESS TO SEPARATE MIXTURES OF ENANTIOMERIC ARYLPROPIONIC ACIDS

The invention concerns a process to separate mixtures of enantiomeric arylpropionic acids and to obtain one of the enantiomeric forms of the acid, by reacting the mixture with a chiralic base in an inert solvent to produce a diastereoisomeric salt from which the desired acid enantiomer is removed.

It is known that the analgesic and anti-rheumatic effects of enantiomers is greater than that of racemic 2-arylpropionic acids. The enantiomeric form shows a higher therapeutic activity than the other form.

U.S. Pat. No. 4,209,638 describes a process to increase the proportion of a desired enantiomer of a 2-arylpropionic acid. In this process, a mixture of a salt of the 2-arylpropionic acid and an inert, liquid, organic diluting agent are heated to at least 80° C. Sufficient salt is used so that a portion does not dissolve in the diluting agent. The mixture is heated until a portion of the optical isomer of the acid component is split into its enantiomer by the formation of salt. The acid component is then removed.

Besides large quantities of solvents, this process requires relatively high temperatures and, in addition, certain portions of the process must be carried out under pressure. Despite this, the purity of the final product leaves much to be desired. The process is both space and time consuming and therefore becomes problematic when it is adapted to large-scale, production environments.

It is the purpose of the invention to create a process as described at the outset of this document, which has substantially better space and time factors than the known process but, at the same time, produces a good yield of optically very pure material.

The task is achieved by the initially described process in that the reaction to a diastereoisomeric salt takes place in a polar solvent, the salt obtained therefrom is purified by several crystallizations, the purified salt is then split in dilute mineral acid and the desired enantiomeric form is thus obtained.

Embodiments of the process are described in the subclaims.

Surprisingly, and against the general point of view, it was discovered that the use of a polar solvent produced far better results than the use of apolar solvents. Contrary to the opinions in the field, no great quantity of solvent was required and, using the smallest volume and shortest reaction time, high yields of a very optically pure product were obtained.

The process basically follows the procedure outlined below.

X moles of 2-arylpropionic acid are treated with X/2 moles of the chiralic base in the corresponding portion of solvent. Stirring is continued for approx. 30 minutes after the addition of the base. After possible cooling, the diastereoisomeric salt is removed from the solvent and crystallized several times—preferably from 1 to 4 times. The thus purified diastereoisomer is suspended in water, split with hydrochloric acid and removed from the aqueous solution.

The ratio between diastereoisomeric salt and solvent is in the range between 1:0.2 to 1:100, preferably between 1:0.6 and 1:15 (G/V).

It is preferable that the process be carried out under recyclic conditions. With sensitive bases, the process can be carried out in an atmosphere of safety gas such as nitrogen.

The Operating temperature for the process lies between room temperature and the boiling points of the employed solutions.

The process in accordance with the invention is described further by two examples.

EXAMPLE 1

115 kg of ibuprofen (537.4 moles) were dissolved in 300 l 2-propanol in a heated mixing chamber. When the solution reached approx. 60° C., 33.8 kg of phenylethylamine dissolved in 87 l of 2-propanol were added. After the addition was completed, the mixture was stirred for an additional 30 minutes at its boiling point and, under continuous stirring, the mixture was brought to room temperature. The precipitated diastereoisomer was pressed out and washed with approx. 20 l of ice-cold 2-propanol.

Yield: 64.8 kg of diastereoisomer (71% of the theoretical yield) (enantiomeric purity: 89%).

This diastereoisomer was recrystallized out of 343 l of hot ethanol.

Yield: 50.2 kg of diastereoisomer (55% of the theoretical yield) (enantiomeric purity: 95%).

This diastereoisomer was recrystallized out of 281 l of hot ethanol.

Yield: 43.7 kg of diastereoisomer (47.9% of the theoretical yield) (enantiomeric purity: 98%).

This diastereoisomer was recrystallized out of 276 l of hot ethanol.

Yield: 38.2 kg of diastereoisomer (42% of the theoretical yield) (enantiomeric purity: ≧99.5%).

Under stirring, the thus purified diastereoisomer was suspended in 300 l of demineralized water, treated with 13 l of hydrochloric acid (32%), pressed out after 2 hours, neutralized by rinsing with demineralized water and dried.

Yield: 24.1 kg (42% of the theoretical yield)(S)-(+)-ibuprofen (enantiomeric purity: ≧99.5%).

The following table contains detailed information.

Results using ketoprofens and flurbiprofens as well as quinone and cinchonidine are also given.

| Example | Acid | Base | Solvent | Volumetric ratio [g salt/g solution] | Temp. | Yield (approx.) | $[\alpha]_D$ of the acid(1) |
|---|---|---|---|---|---|---|---|
| 3 | 1 | 1 | methyl alcohol | 1:1.4 to 147 | RT b.p. | 30% | +60.4 |
| 4 | 1 | 1 | ethyl alcohol | 1:1.6 to 163 | RT b.p. | 42% | +60.2 |
| 5 | 1 | 1 | 2-propanol | 1:2.7 to 1:12 | RT b.p. | 60% | +60.1 |
| 6 | 1 | 1 | ethyl acetate | 1:16.2 to 1:40 | RT b.p. | 43% | +60.3 |
| 7 | 1 | 1 | ethyl acetate-ethyl alcohol (5 + 1) | 15.5 to 1:9 | RT b.p. | 53% | +60.4 |
| 8 | 1 | 1 | dimethyl formamide | 1:3.1 to 1:11 | RT b.p. | 55% | +60.4 |
| 9 | 1 | 1 | acetone | 1:2.8 to 1:10 | RT b.p. | 48% | +60..3 |
| 10 | 1 | 1 | dimethyl sulfoxide | 1:3.1 to 1:11 | RT b.p. | 41% | +60.4 |

-continued

| Example | Acid | Base | Solvent | Volumetric ratio [g salt/g solution] | Temp. | Yield (approx.) | $[\alpha]_D$ of the acid[1] |
|---|---|---|---|---|---|---|---|
| 11 | I | 1 | monoglyme | 1:3.1 to 1:11 | RT b.p. | 44% | +60.3 |
| 12 | I | 2 | methyl alcohol | 1:0.7 to 1:3 | RT b.p. | 20% | +60.4 |
| 13 | I | 2 | isopropanol | 1:1.0 to 11.5 | RT b.p. | 32% | +60.2 |
| 14 | I | 2 | ethyl alcohol | 1:0.63 to 11 | RT b.p. | 41% | +60.2 |
| 15 | I | 3 | dimethyl formamide | 110 | RT b.p. | 48% | +60.3 |
| 16 | K | 1 | 2-propanol | 1:1.0 to 115 | RT b.p. | 40% | +49.8 |
| 17 | F | 1 | 2-propanol | 1:1.0 to 130 | RT b.p. | 42% | +44.7 |

[1]C = 10% in methanol
Acid: I = ibuprofen K = ketoprofen F = flurbiprofen
Bases 1 = phenylethyl amine 2 = quinine 3 = cinchonidine

EXAMPLE 2

50 kg of ibuprofen (242.4 moles) were dissolved in 80 l of 2-propanol in a heated mixing chamber. 29.4 kg (242.4 moles) of phenylethylamine dissolved in 30 liters of 2-propanol were added to the mixture. After the addition was completed, the mixture was stirred for an additional 30 minutes at its boiling point and was subsequently cooled to approx. 2° to 5° C. The precipitated diastereoisomer was pressed out and twice washed with 20 l of ice-cold 2-propanol.

Yield: 39.7 kg of diastereoisomer (100% of the theoretical yield) (enantiomeric purity: 80%).

After the product was thrice recrystallized out of ethanol and split with hydrochloric acid, as described in example 1, the following yield was obtained: 12.5 kg (50% of the theoretical yield) Enantiomeric purity: 98%.

What is claimed is:

1. A process to separate a mixture of enantiomers of an arylpropionic acid and to obtain a desired enantiomeric form of the acid, comprising: reacting the mixture with a chiralic base in an inert polar solvent to produce a diastereoisomeric salt, wherein the chiralic base is a member selected from the group consisting of phenylethyl amine, quinoline alkaloid and ephedrine base; purifying the diastereoisomeric salt by multiple crystallization; splitting the purified diastereoisomeric salt in dilute mineral acid; and removing the desired enantiomer from the diastereoisomeric salt.

2. A process in accordance with claim 1, wherein the mixture is a racemic mixture of the arylpropionic acid or a mixture of two enatiomers thereof.

3. A process in accordance with claim 1, wherein the remnant from the split of the diastereoisomeric salt from which the desired acid enantiomer has been removed is directly processed or repeatedly treated with the chiralic base in order to increase the enantiomeric portion.

4. A process in accordance with claim 1, wherein the proportion of the chiralic base is X/2 to X moles, with respect to X moles of the arylpropionic acid.

5. A process in accordance with claim 1, wherein the reaction to produce the diastereoisomeric acid is carried out at a temperature between room temperature and the boiling point of the polar solvent.

6. A process in accordance with claim 1, wherein a lower alcohol, ether or ester or a mixture thereof is employed as the polar solvent.

7. A process in accordance with claim 1, wherein the arylpropionic acid is a member selected from the group consisting of ibuprofen, ketoprofen and flurbiprofen.

8. A process in accordance with claim 1, wherein the ratio between the diastereoisomeric salt and the polar solvent lies in the range 1:0.2 to 1:100.

9. A process in accordance with claim 1, wherein the process is carried out under recyclic conditions.

10. A process in accordance with claim 1, wherein the process is carried out in a safety gas atmosphere.

11. A process in accordance with claim 1, wherein the arylpropionic acid is ibuprofen, and the multiple crystallization comprises a first precipitation and further concentration, and the ibuprofen is released from the diastereoisomeric salt after the first precipitation and the further concentration is achieved by recrystallization, whereby the first crystalline fraction consists of an optically active arylpropionic acid mixture and the enriched mother liquor contains the corresponding optical antipode.

12. A process in accordance with claim 2, wherein a lower alcohol, ether or ester or a mixture thereof is employed as the polar solvent.

13. A process in accordance with claim 3, wherein a lower alcohol, ether or ester or a mixture thereof is employed as the polar solvent.

14. A process in accordance with claim 4, wherein a lower alcohol, ether or ester or a mixture thereof is employed as the polar solvent.

15. A process in accordance with claim 5, wherein a lower alcohol, ether or ester or a mixture thereof is employed as the polar solvent.

* * * * *